United States Patent
Schoenhagen et al.

(10) Patent No.: US 11,475,561 B2
(45) Date of Patent: Oct. 18, 2022

(54) AUTOMATED IDENTIFICATION OF ACUTE AORTIC SYNDROMES IN COMPUTED TOMOGRAPHY IMAGES

(71) Applicant: THE CLEVELAND CLINIC FOUNDATION, Cleveland, OH (US)

(72) Inventors: Paul Schoenhagen, Cleveland, OH (US); Po-Hao Chen, Cleveland, OH (US); David Piraino, Cleveland, OH (US); Nancy Obuchowski, Cleveland, OH (US)

(73) Assignee: THE CLEVELAND CLINIC FOUNDATION, Cleveland, OH (US)

( * ) Notice: Subject to any disclaimer, the term of this patent is extended or adjusted under 35 U.S.C. 154(b) by 299 days.

(21) Appl. No.: 16/906,167

(22) Filed: Jun. 19, 2020

(65) Prior Publication Data
US 2020/0402232 A1    Dec. 24, 2020

Related U.S. Application Data

(60) Provisional application No. 62/863,895, filed on Jun. 20, 2019.

(51) Int. Cl.
*G06T 7/00* (2017.01)
*A61B 6/12* (2006.01)
(Continued)

(52) U.S. Cl.
CPC ............ *G06T 7/0012* (2013.01); *A61B 6/032* (2013.01); *A61B 6/12* (2013.01); *A61B 6/469* (2013.01);
(Continued)

(58) Field of Classification Search
CPC .......... A61B 6/032; A61B 6/12; A61B 6/469; A61B 6/504; A61B 6/5217; G06K 9/6271;
(Continued)

(56) References Cited

U.S. PATENT DOCUMENTS 9,589,211 B2 *    3/2017    Lay ........................ G06T 11/206

FOREIGN PATENT DOCUMENTS

| CN | 108764221 A | 11/2018 |
| CN | 109035255 A | 12/2018 |
| EP | 3432215 A1 | 1/2019 |

OTHER PUBLICATIONS

Cowie, Martin R., Catherine E. Chronaki, and Panos Vardas. "e-Health innovation: time for engagement with the cardiology community." European heart journal 34.25 (2013): 1864-1868.
(Continued)

*Primary Examiner* — Manucheher Rahmjoo
(74) *Attorney, Agent, or Firm* — Tarolli, Sundheim, Covell & Tummino LLP (57) ABSTRACT

Systems and methods are provided for automated identification of acute aortic syndromes in computed tomography images. A region of interest in a chest of a patient is imaged via a computed tomography (CT) scanner to provide images at a plurality of locations. The region of interest includes one of an ascending aorta, an aortic arch, and a descending aorta of the patient. For each of the plurality of locations within the region of interest, a value representing a variation in radiodensity values within the location is determined from the image to provide a set of variation values. A parameter representing a likelihood that the patient is experiencing an acute aortic syndrome is determined via a derived model from the set of variation values. The parameter representing the likelihood that the patient is experiencing the acute aortic syndrome is provided to a user at an associated output device.

17 Claims, 3 Drawing Sheets

(51) Int. Cl.

| | |
|---|---|
| *A61B 6/03* | (2006.01) |
| *A61B 6/00* | (2006.01) |
| *G16H 10/60* | (2018.01) |
| *G16H 50/30* | (2018.01) |
| *G16H 50/20* | (2018.01) |
| *G06V 10/40* | (2022.01) |

(52) U.S. Cl.
CPC .............. *G06V 10/40* (2022.01); *G16H 10/60* (2018.01); *G16H 50/20* (2018.01); *G16H 50/30* (2018.01); *G06T 2207/10081* (2013.01); *G06T 2207/30004* (2013.01)

(58) Field of Classification Search
CPC . G06T 2207/10081; G06T 2207/30004; G06T 2207/30048; G06T 2207/30101; G06T 7/0012; G06V 10/40; G06V 10/82; G06V 2201/031; G16H 10/60; G16H 30/40; G16H 50/20; G16H 50/30
See application file for complete search history.

(56) References Cited

OTHER PUBLICATIONS

Boyd DR, Dunea MM, Flashner BA. The Illinois plan for a statewide system of trauma centers. J Trauma. Jan. 1973;13(1):24-31. doi: 10.1097/00005373-197301000-00005. PMID: 4687243.

Crowley RA, Hudson F, Scanlan E, Gill W, Lally RJ, Long W, Kuhn AO. An economical and proved helicopter program for transporting the emergency critically ill and injured patient in Maryland. J Trauma. Dec. 1973;13(12):1029-38. doi: 10.1097/00005373-197312000-00001. PMID: 4753485.

Harris KM, Strauss CE, Duval S, Unger BT, Kroshus TJ, Inampudi S, Cohen JD, Kapsner C, Boland LL, Eales F, Rohman E, Orlandi QG, Flavin TF, Kshettry VR, Graham KJ, Hirsch AT, Henry TD. Multidisciplinary standardized care for acute aortic dissection: design and initial outcomes of a regional care model. Circ Cardiovasc Qual Outcomes. Jul. 2010;3(4):424-30. doi: 10.1161/CIRCOUTCOMES.109.920140. PMID: 20647576.

Henry Madison JD, Menssen KM, Mooney MR, Newell MC, Pedersen WR, Poulose AK, Traverse JH, Unger BT, Wang YL, Larson DM. A regional system to provide timely access to percutaneous coronary intervention for ST-elevation myocardial infarction. Circulation. Aug. 14, 2007;116(7):721-8. doi: 10.1161/CIRCULATIONAHA.107.694141. Epub Aug. 1, 2007. PMID: 17673457.

Ting HH, Rihal CS, Gersh BJ, Haro LH, Bjerke CM, Lennon RJ, Lim CC, Bresnahan JF, Jaffe AS, Holmes DR, Bell MR. Regional systems of care to optimize timeliness of reperfusion therapy for ST-elevation myocardial infarction: the Mayo Clinic STEMI Protocol. Circulation. Aug. 14, 2007;116(7):2729-36. doi: 10.1161/CIRCULATIONAHA.107.699934. Epub Aug. 1, 2007. PMID: 17673456.

Jollis JG, Roettig ML, Aluko AO, Anstrom KJ, Applegate RJ, Babb JD, Berger PB, Bohle DJ, Fletcher SM, Garvey JL, Hathaway WR, Hoekstra JW, Kelly RV, Maddox WT Jr, Shiber JR, Valeri FS, Watling BA, Wilson BH, Granger CB; Reperfusion of Acute Myocardial Infarction in North Carolina Emergency Departments (RACE) Investigators. Implementation of a statewide system for coronary reperfusion for ST-segment elevation myocardial infarction. JAMA. Nov. 28, 2007;298(20):2371-80. doi: 10.1001/jama.298.20.joc70124. Epub Nov. 4, 2007. PMID: 17982184.

Lamonte MP, Bahouth MN, Magder LS, Alcorta RL, Bass RR, Browne BJ, Floccare DJ, Gaasch WR; Emergency Medicine Network of the Maryland Brain Attack Center. A regional system of stroke care provides thrombolytic outcomes comparable with the NINDS stroke trial. Ann Emerg Med. Sep. 2009;54(3):319-27. doi: 10.1016/j.annemergmed.2008.09.022. Epub Dec. 19, 2008. PMID: 19101059.

Aggarwal B, Raymond C, Jacob J, Kralovic D, Kormos K, Holloway D, Menon V. Transfer of patients with suspected acute aortic syndrome. Am J Cardiol. Aug. 1, 2013;112(3):430-5. doi: 10.1016/j.amjcard.2013.03.049. Epub May 10, 2013. PMID: 23668639.

Raymond CE, Aggarwal B, Schoenhagen P, Kralovic DM, Kormos K, Holloway D, Menon V. Prevalence and factors associated with false positive suspicion of acute aortic syndrome: experience in a patient population transferred to a specialized aortic treatment center. Cardiovasc Diagn Ther. Dec. 2013;3(4):196-204. doi: 10.3978/j.issn.2223-3652.2013.12.06. PMID: 24400203; PMCID: PMC3878122.

Aggarwal, Bhuvnesh, et al. "Transfer metrics in patients with suspected acute aortic syndrome." Circulation: Cardiovascular Quality and Outcomes 7.5 (2014): 780-782.

Schoenhagen, Paul, Mathis Zimmermann, and Juergen Falkner. "Advanced 3-D analysis, client-server systems, and cloud computing—Integration of cardiovascular imaging data into clinical workflows of transcatheter aortic valve replacement." Cardiovascular diagnosis and therapy 3.2 (2013): 80.

Schoenhagen P, Falkner J, Piraino D. Transcatheter aortic valve repair, imaging, and electronic imaging health record. Curr Cardiol Rep. Jan. 2013;15(1):319. doi: 10.1007/s11886-012-0319-1. PMID: 23250656.

Matar R, Renapurkar R, Obuchowski N, Menon V, Piraino D, Schoenhagen P. Utility of hand-held devices in diagnosis and triage of cardiovascular emergencies. Observations during implementation of a PACS-based system in an acute aortic syndrome (AAS) network. J Cardiovasc Comput Tomogr. Nov.-Dec. 2015;9(6):524-33. doi: 10.1016/j.jcct.2015.07.013. Epub Aug. 3, 2015. PMID: 26277273.

Deo RC. Machine Learning in Medicine. Circulation. Nov. 17, 2015;132(20):1920-30. doi: 10.1161/CIRCULATIONAHA.115.001593. PMID: 26572668; PMCID: PMC5831252.

Liang, Mingzhu, et al. "Low-dose CT screening for lung cancer: computer-aided detection of missed lung cancers." Radiology 281.1 (2016): 279-288.

Singal, Amit G., et al. "Machine learning algorithms outperform conventional regression models in predicting development of hepatocellular carcinoma." The American journal of gastroenterology 108.11 (2013): 1723.

Mjolsness, Eric, and Dennis DeCoste. "Machine learning for science: state of the art and future prospects." science 293.5537 (2001): 2051-2055.

Bakkar, Nadine, et al. "Artificial intelligence in neurodegenerative disease research: use of IBM Watson to identify additional RNA-binding proteins altered in amyotrophic lateral sclerosis." Acta neuropathologica 135.2 (2018): 227-247.

Huynh, Quan L., et al. "Predictive score for 30-day readmission or death in heart failure." JAMA cardiology 1.3 (2016): 362-364.

Motwani, Manish, et al. "Machine learning for prediction of all-cause mortality in patients with suspected coronary artery disease: a 5-year multicentre prospective registry analysis." European heart journal 38.7 (2017): 500-507.

Schoenhagen, Paul, et al. "Online network of subspecialty aortic disease experts: Impact of "cloud" technology on management of acute aortic emergencies." (2016): 39-42.

Schoenhagen, Paul, and Neil Mehta. "Big data, smart computer systems, and doctor-patient relationship." European heart journal 38.7 (2017): 508-510.

Kovacs, Tamás, et al. "Automatic segmentation of the aortic dissection membrane from 3D CTA images." International Workshop on Medical Imaging and Virtual Reality. Springer, Berlin, Heidelberg, 2006.

Lopez-Linares, Karen, et al. "Fully automatic detection and segmentation of abdominal aortic thrombus in post-operative CTA images using deep convolutional neural networks." Medical image analysis 46 (2018): 202-214.

Dehghan, Ehsan, Hongzhi Wang, and Tanveer Syeda-Mahmood "Automatic detection of aortic dissection in contrast-enhanced CT." 2017 IEEE 14th International Symposium on Biomedical Imaging (ISBI 2017). IEEE, 2017.

Krissian, Karl, et al. "Semi-automatic segmentation and detection of aorta dissection wall in MDCT angiography." Medical image analysis 18.1 (2014): 83-102.

(56) References Cited

OTHER PUBLICATIONS

Maiora, Josu, and Manuel Graña. "Abdominal cta image analisys through active learning and decision random forests: Aplication to aaa segmentation." The 2012 international joint conference on neural networks (IJCNN). IEEE, 2012.
Hagan, Peter G., et al. "The International Registry of Acute Aortic Dissection (IRAD): new insights into an old disease." Jama 283.7 (2000): 897-903.
Bonow, Robert O., et al. Braunwald's heart disease e-book: A textbook of cardiovascular medicine. Elsevier Health Sciences, 2011.
Rogers, Adam M., et al. "Sensitivity of the aortic dissection detection risk score, a novel guideline-based tool for identification of acute aortic dissection at initial presentation: results from the international registry of acute aortic dissection." Circulation 123.20 (2011): 2213-2218.

\* cited by examiner

AUTOMATED IDENTIFICATION OF ACUTE AORTIC SYNDROMES IN COMPUTED TOMOGRAPHY IMAGES

RELATED APPLICATIONS

This application claims priority from U.S. Provisional Application No. 62/863,895, filed 20 Jun. 2019, the subject matter of which is incorporated herein by reference in its entirety.

TECHNICAL FIELD

This invention relates to diagnostic imaging, and more specifically, to automated identification of acute aortic syndromes in computed tomography images.

BACKGROUND

The aorta is the main arterial blood vessel transporting the oxygenated blood from the lung through the left heart pumping chamber to the different organ systems including the brain, the heart muscle, the visceral organs, and the limbs. The aorta measures about three centimeters in diameter, with blood flowing in the lumen. The lumen is contained by the aortic wall, which has several layers, including, in order from the lumen to outer aspect of wall, the intima, the media, and the adventitia. Acute aortic syndromes (AAS) occur with an incidence estimated at five to thirty per one million people per year, amounting to about 10,000 cases per year in the United States. Examples of AAS include class I and class II aortic dissections as well as penetrating aortic ulcers. AAS has a high early mortality with the death rate in acute dissection as high as one percent per hour during the first twenty-four hours. Therefore prompt diagnosis and emergency treatment are critical.

Aortic dissection is defined by acute separation of the layers of the aortic wall, with the blood stream entering the aortic wall, creating a 'false lumen' within the wall, typically in the media. The remaining wall layers separating the true and false lumen are called the dissection flap. In communicating, or class I, dissections, there is blood flow in the true and false lumen, separated by a dissection flap. In contrast, in intramural hematomas, or class II dissections, the blood in the false lumen is stagnant or thrombosed.

Triage of patients with suspected AAS requires definitive imaging, and contrast enhanced computed tomography (CT) is the most common diagnostic test, with very high diagnostic accuracy. Imaging of aortic dissection with computed tomography (CT) is typically performed after iodine-based contrast injection into the blood stream, generally via an arm vein. Blood enhanced with contrast is brighter than unenhanced blood on the CT image due to increased radiodensity. Radiodensity is generally defined by Hounsfield Units (HU). Bright, contrast-enhanced blood has a Hounsfield unit of about 350 HU, while unenhanced blood has a HU of about 30 units. In communicating dissections, the contrast enhances the flowing blood in the true and false lumen, and therefore the dissection flap between the true and false lumen is visible. In most cases, the density of enhancement is different between the true and false lumen, reflecting how vigorously blood enters the false lumen, but also the timing of contrast injection. In contrast, in intramural hematomas, the false lumen does not enhance with contrast, because there is no blood flow in the false lumen. Therefore the dissection flap', which has similar HU than the thrombosed false lumen, is not visible.

Once an acute aortic syndrome is identified, further management is addressed in multidisciplinary treatment teams. Many patients with acute aortic dissection are therefore transferred to a tertiary care center with a staff experienced in managing aortic dissection and its complications. Within large healthcare systems, regional treatment networks have been established to coordinate diagnosis, triage, and treatment between initial point of contact (e.g., a local emergency room) and central specialized centers experienced in definitive pharmacologic, interventional, or surgical treatment. In these networks, a group of specialists remotely directs the initial diagnosis and triage of patients in a larger geographic area.

As described above, imaging has a critical role in the early assessment. Computed tomography is typically performed and interpreted at the initial point of access, which could include a variety of environments including the local emergency department, out-patient imaging centers, or inpatient imaging centers. While knowledge about AAS is universally high, false positive and negative reports and delayed reporting are a reality. In an investigation of the prevalence and etiology of false positive diagnoses in patients transferred to a tertiary referral center for suspected AAS, our group found false positive suspicion of dissection in seventeen of one hundred fifty (11.3%) consecutive patients transferred for suspected AAS from community emergency departments directly to the cardiac intensive care unit. False-positive activation was driven primarily by uncertainty secondary to motion artifact of the ascending aorta and the presence of complex anatomy after previous aortic intervention.

Unfortunately, interpretation of chest CT angiography requires a turnaround time of minutes to tens of minutes even under the best of circumstances, due to the time necessary for scanner equipment to process CT images and upload them to a server, the time for a technician to verify the image quality, and the time necessary for the radiologist to review the image. Further, specifically during 'on-call' hours, the imaging specialist may not be in immediate vicinity of a workstation, further delaying interpretation of the CT image.

SUMMARY

In accordance with one aspect of the invention, a method is provided for automated identification of acute aortic syndromes in computed tomography images. A region of interest in a chest of a patient is imaged via a computed tomography (CT) scanner to provide images at a plurality of locations. The region of interest includes one of an ascending aorta, an aortic arch, and a descending aorta of the patient. For each of the plurality of locations within the region of interest, a value representing a variation in radiodensity values, such as Hounsfield unit (HU) values within the location is determined from the image to provide a set of variation values. A parameter representing a likelihood that the patient is experiencing an acute aortic syndrome is determined via a derived model from the set of variation values. The parameter representing the likelihood that the patient is experiencing the acute aortic syndrome is provided to a user at an associated output device.

In accordance with another aspect of the invention, a system includes a processor and a non-transitory computer readable medium storing executable instructions executable by the processor. When executed by the processor, the executable instructions provide a scanner interface, a feature extractor, a derived model, and a user interface. The scanner interface receives an image of a region of interest in a chest of a patient from a computed tomography (CT) scanner. The region of interest includes one of the ascending aorta, aortic arch, and descending aorta of the patient. The feature extractor determines, for each of a plurality of locations within the region of interest, a value representing a variation in radiodensity values, such as Hounsfield Unit (HU) values within the location to provide a set of variation values. The derived model determines, from at least the set of variation values, a parameter representing a likelihood that the patient is experiencing an acute aortic syndrome. The user interface provides the parameter presenting the likelihood that the patient is experiencing the acute aortic syndrome to an associated output device.

In accordance with yet another aspect of the invention, a system includes a processor, a computed tomography (CT) scanner, and a non-transitory computer readable medium storing executable instructions executable by the processor. When executed by the processor, the executable instructions provide a scanner interface, a feature extractor, a derived model, and a user interface. The scanner interface receives an image of a region of interest in a chest of a patient from a computed tomography (CT) scanner. The region of interest includes one of the ascending aorta, aortic arch, and descending aorta of the patient. The feature extractor determines, for each of a plurality of locations within the region of interest, a range of Hounsfield unit (HU) values within the location to provide a set of range values. The derived model determines, from at least the set of range values, a parameter representing a likelihood that the patient is experiencing an acute aortic syndrome. The user interface provides the parameter presenting the likelihood that the patient is experiencing the acute aortic syndrome to an associated output device.

DETAILED DESCRIPTION

An "average," as used herein, can be any measure of central tendency, including but not limited to, an arithmetic mean, a geometric mean, a median, and a mode.

A "value representing a variation," as used herein, can be any statistical measure of dispersion for a set of values, including but not limited to, a standard deviation, a mean absolute variation, a variance, an interquartile range, a range, a coefficient of variation, and a difference between values representing any two selected percentiles of the data set.

A "clinical parameter", as used herein, is any continuous or categorical parameter that is relevant to clinical diagnosis of a patient. Clinical parameters can include, but are not limited to, parameters representing a medical history of the patient, characteristics of the patient, such as sex and age, clinical measurements, such as aortic diameter, and current or past values for the biometric parameters of the patient, such as blood pressure, weight, body temperature, and similar values.

A "known clinical outcome," as used herein, is a determination, by a medical professional, of the presence or absence of an acute aortic syndrome generally and/or the presence or absence of a specific type, class, or location of an acute aortic syndrome.

A "derived model," as used herein, is a model that uses a statistical aggregation of data from patients having known clinical outcomes to predict an unknown outcome for a patient from one or more values extracted from one or more CT images of the patient.

A "mid-ascending aorta," as used herein, is defined the midpoint between the sinotubular junction and the proximal aortic arch.

A "radiodensity value," as used herein, includes any metric of radiodensity or radiolucency obtained from a medical image.

Systems and methods are provided herein for automated identification of acute aortic syndromes in computed tomography (CT) images. The disclosed systems and methods extract data representing radiodensity values, such as Hounsfield Unit (HU) values, in CT images of an aorta of a patient and utilize derived models to provide an immediate identification of an acute aortic syndrome without the need for expert intervention, allowing for rapid intervention. For example, the automated determination can be used to initiate surgical or pharmacological intervention, begin transfer of patients indicated to have AAS to specialized treatment centers, or prioritize review of the CT imaging for the radiologist.

Figure 1:
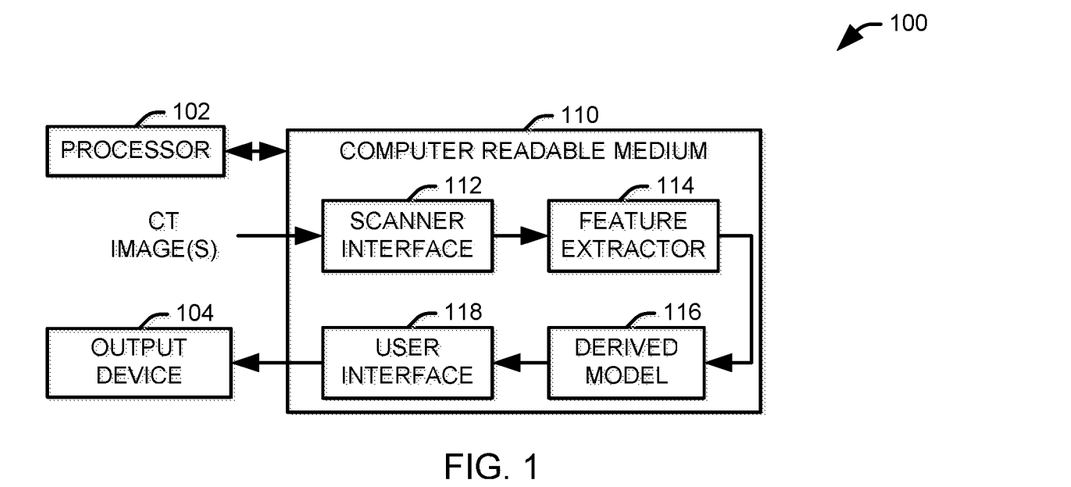
FIG. 1 illustrates an example of a system for automated identification of acute aortic syndromes in computed tomography images.

FIG. 1 illustrates an example of a system 100 for automated identification of acute aortic syndromes in computed tomography images. The system 100 includes a processor 102, an output device 104, and a non-transitory computer readable medium 110 storing executable instructions executable by the processor. The executable instructions stored at the non-transitory computer readable medium 110 include a scanner interface 112 that receives CT images of a region of interest in a chest of a patient from a computed tomography (CT) scanner. The region of interest can include one or more of the ascending aorta, aortic arch, and descending aorta of the patient. It will be appreciated that the scanner interface 112 can receive the CT images via a direct connection with the CT imager, for example, via parallel or serial bus connection, or via a network connection. In one example, the scanner interface 112 can retrieve the images from a physical or cloud server via the network connection. In some implementations, the system 100 can be integral with the CT scanner, and the scanner interface 112 can simply include instructions for conditioning a captured CT image for further analysis.

A feature extractor 114 determines a value representing a variation in radiodensity values within each of a plurality of locations within the region of interest to provide a set of variation values. For example, the plurality of locations can be represented as a set of cross-sectional planes within one or more of the ascending aorta, the aortic arch, and the descending aorta. In one implementation, the feature extractor 114 can determine, for each location, a plurality of representative values and determine a statistical measure of dispersion, such as the range or standard deviation, across the plurality of values. In one example, each location is divided into a plurality of regions, and a representative value is extracted from each region, for example, as a measure of central tendency for all or a portion of the region. For example, a subregion lying entirely within each region can be defined and an average value for the subregion can be used as the representative value.

The derived model 116 determines, from at least the set of variation values, a parameter representing a likelihood that the patient is experiencing an acute aortic syndrome. It will be appreciated that the parameter can be categorical, for example representing a presence, location, type, or class of an AAS or a range of likelihoods that the patient had an AAS in one of those categories, or continuous, for example, representing the likelihood that the patient has an AAS generally or a specific location, type, or class of AAS. In one example, the derived model 116 is a decision tree in that can determine at least the presence of an AAS from the set of variation values, and, in some examples, one or more of the location, type, and class of the AAS. The output of the derived model 116 can be provided to a user interface 118 that provides the parameter presenting the likelihood that the patient is experiencing the acute aortic syndrome to the output device 104.

Figure 2:
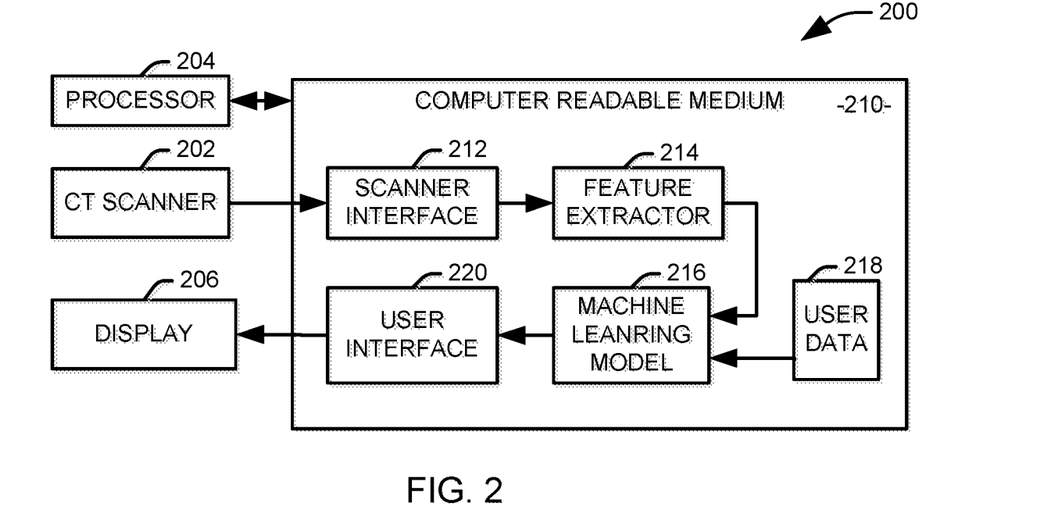
FIG. 2 illustrates another example of a system for automated identification of acute aortic syndromes in computed tomography images.

FIG. 2 illustrates another example of a system 200 for automated identification of acute aortic syndromes in computed tomography images. The system 200 includes a computed tomography (CT) scanner 202, a processor 204, a display 206, and a non-transitory computer readable medium 210 storing executable instructions executable by the processor. The executable instructions stored at the non-transitory computer readable medium 210 include a scanner interface 212 that receives CT images of a region of interest in a chest of a patient from a computed tomography (CT) scanner.

A feature extractor 214 determines a value representing a variation in Hounsfield Unit (HU) values within each of a plurality of locations within the region of interest to provide a set of variation values. The plurality of locations can be selected as a set of cross-sectional planes within one or more of the ascending aorta, the aortic arch, and the descending aorta. In the illustrated implementation, a first cross-sectional plane of the set of cross-sectional planes is selected to coincide with the mid-ascending aorta, a second cross-sectional plane of each of the set of cross-sectional planes is selected to coincide with a point that is a predetermined distance above the mid ascending aorta, and a third cross-sectional plane of each of the set of cross-sectional planes is selected to coincide with a point that is the predetermined distance below the mid ascending aorta. The predetermined distance can vary with the specific implementation, but in some examples, will fall within a range between one and two centimeters. In one example, the predetermined distance is 1.5 centimeters.

The feature extractor 214 determines, for each location, a plurality of representative values and determine a statistical measure of dispersion, such as the range or standard deviation, across the plurality of values. In one example, each location is divided into a plurality of regions, and a representative value is extracted from each region, for example, as an average for all or a portion of the region. For example, a subregion lying entirely within each region can be defined and an average value for the subregion can be used as the representative value. In the illustrated implementation, the range of the plurality of representative HU values is used, calculated as the maximum variation between any two of the representative values.

A machine learning model 216 determines, from at least the set of variation values, a parameter representing a likelihood that the patient is experiencing an acute aortic syndrome (AAS). It will be appreciated that the parameter can be continuous, expressed as a likelihood that the patient has an AAS, the likelihood that the patient has an AAS in a specific location (e.g., an AAS related to changes in the ascending aorta), a specific type (e.g., penetrating aortic ulcer or aortic dissection), or specific class of AAS (e.g., class II aortic dissection). The parameter can also be categorical, for example, representing ranges of likelihoods of an AAS generally or a specific type, class, or location of AAS, or the likely presence of an AAS generally or a specific type, class, or location of AAS. The output of the machine learning model is then provided to the user at the display 220 via a user interface 220.

The machine learning model can also utilize clinical parameters extracted from user data 218 stored either locally or at a remote server (not shown), including, for example, age, sex, genomic data, aortic diameter, family history, blood pressure, nutritional information, medication intake, and relevant medical history. Relevant medical conditions can include, but are not limited to, pregnancy, a history of atherosclerosis, a history of aortic aneurysm, a bicuspid aortic valve, aortic coarcation, and genetic conditions such as Turner's Syndrome, Marfan's Syndrome, other connective tissue disorders, and various inflammatory or infectious conditions.

The machine learning model 216 can utilize one or more pattern recognition algorithms, each of which analyze the extracted features or a subset of the extracted features to assign a continuous or categorical parameter to the user. Where multiple classification or regression models are used, an arbitration element can be utilized to provide a coherent result from the plurality of models. The training process of a given classifier will vary with its implementation, but training generally involves a statistical aggregation of training data into one or more parameters associated with the output class. The training process can be accomplished on a remote system and/or the local device, and can be achieved in a federated or non-federated fashion. For rule-based models, such as decision trees, domain knowledge, for example, as provided by one or more human experts, can be used in place of or to supplement training data in selecting rules for classifying a user using the extracted features. Any of a variety of techniques can be utilized for the classification algorithm, including support vector machines, regression models, self-organized maps, fuzzy logic systems, data fusion processes, boosting and bagging methods, rule-based systems, or artificial neural networks.

For example, an SVM classifier can utilize a plurality of functions, referred to as hyperplanes, to conceptually divide boundaries in the N-dimensional feature space, where each of the N dimensions represents one associated feature of the feature vector. The boundaries define a range of feature values associated with each class. Accordingly, an output class and an associated confidence value can be determined for a given input feature vector according to its position in feature space relative to the boundaries. In one implementation, the SVM can be implemented via a kernel method using a linear or non-linear kernel.

An ANN classifier comprises a plurality of nodes having a plurality of interconnections. The values from the feature vector are provided to a plurality of input nodes. The input nodes each provide these input values to layers of one or more intermediate nodes. A given intermediate node receives one or more output values from previous nodes.

The received values are weighted according to a series of weights established during the training of the classifier. An intermediate node translates its received values into a single output according to a transfer function at the node. For example, the intermediate node can sum the received values and subject the sum to a binary step function. A final layer of nodes provides the confidence values for the output classes of the ANN, with each node having an associated value representing a confidence for one of the associated output classes of the classifier.

Many ANN classifiers are fully-connected and feedforward. A convolutional neural network, however, includes convolutional layers in which nodes from a previous layer are only connected to a subset of the nodes in the convolutional layer. Recurrent neural networks are a class of neural networks in which connections between nodes form a directed graph along a temporal sequence. Unlike a feedforward network, recurrent neural networks can incorporate feedback from states caused by earlier inputs, such that an output of the recurrent neural network for a given input can be a function of not only the input but one or more previous inputs. As an example, Long Short-Term Memory (LSTM) networks are a modified version of recurrent neural networks, which makes it easier to remember past data in memory.

A rule-based classifier applies a set of logical rules to the extracted features to select an output class. Generally, the rules are applied in order, with the logical result at each step influencing the analysis at later steps. The specific rules and their sequence can be determined from any or all of training data, analogical reasoning from previous cases, or existing domain knowledge. One example of a rule-based classifier is a decision tree algorithm, in which the values of features in a feature set are compared to corresponding threshold in a hierarchical tree structure to select a class for the feature vector. A random forest classifier is a modification of the decision tree algorithm using a bootstrap aggregating, or "bagging" approach. In this approach, multiple decision trees are trained on random samples of the training set, and an average (e.g., mean, median, or mode) result across the plurality of decision trees is returned. For a classification task, the result from each tree would be categorical, and thus a modal outcome can be used.

Figure 3:
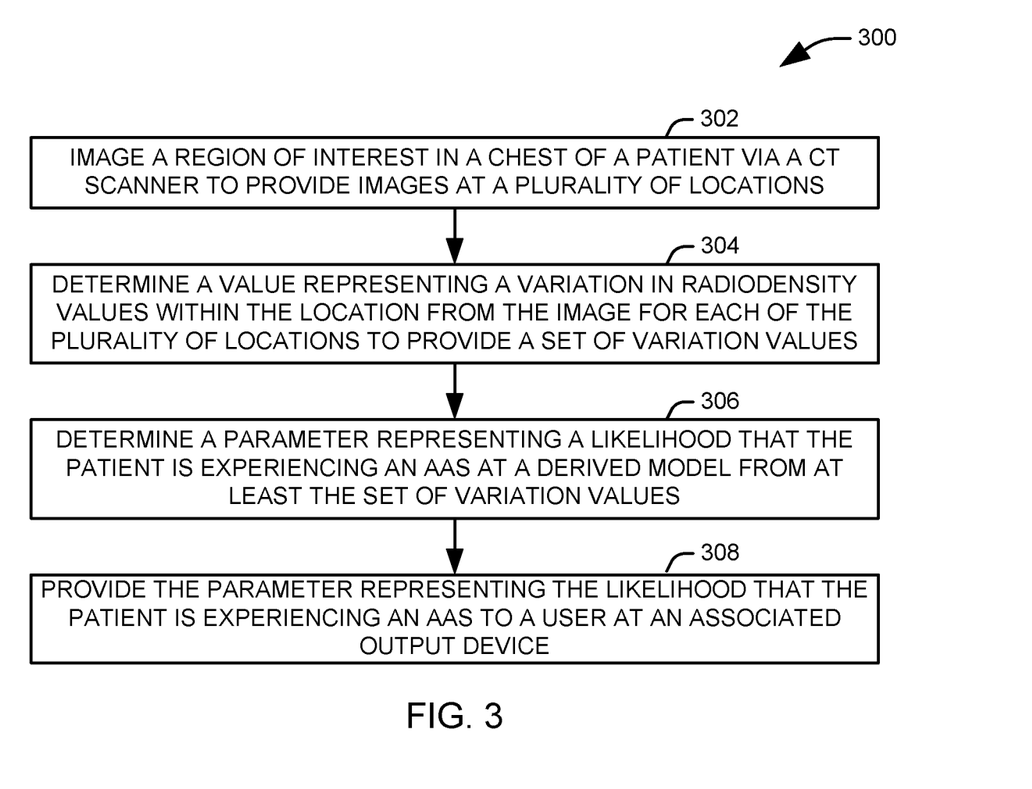
FIG. 3 illustrates one example of a method for automated identification of acute aortic syndromes in computed tomography images.
Figure 4:
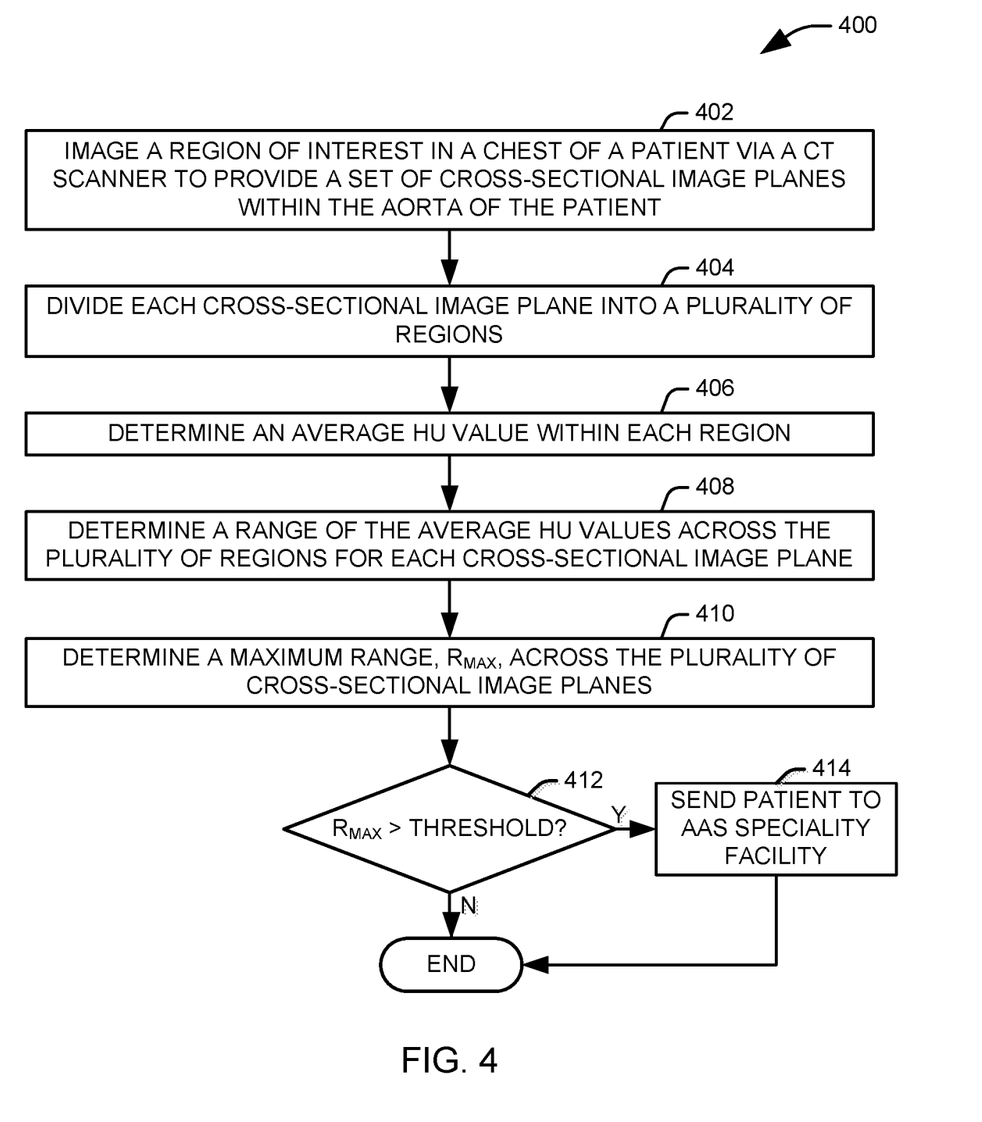
FIG. 4 illustrates one example of a method for automated identification of acute aortic syndromes in computed tomography images.

In view of the foregoing structural and functional features described above, example methods will be better appreciated with reference to FIGS. 3 and 4. While, for purposes of simplicity of explanation, the example method of FIGS. 3 and 4 is shown and described as executing serially, it is to be understood and appreciated that the present examples are not limited by the illustrated order, as some actions could in other examples occur in different orders, multiple times and/or concurrently from that shown and described herein. Moreover, it is not necessary that all described actions be performed to implement a method.

FIG. 3 illustrates one example of a method 300 for automated identification of acute aortic syndromes in computed tomography images. At 302, a region of interest in a chest of a patient is imaged via a computed tomography (CT) scanner to provide images at a plurality of locations. The region of interest includes one or more of an ascending aorta, an aortic arch, and a descending aorta of the patient. At 304, for each of the plurality of locations within the region of interest, a value representing a variation in radiodensity values, such as Hounsfield unit (HU) values within the location is determined from the image to provide a set of variation values. In one example, the plurality of locations are defined as a set of cross-sectional planes within one or more of the ascending aorta, the aortic arch, and the descending aorta. For example, a first cross-sectional plane of the set of cross-sectional planes can be selected to coincide with a mid-ascending aorta, a second cross-sectional plane of the set of cross-sectional planes can be selected to coincide with a point that is a predetermined distance above the mid ascending aorta, and a third cross-sectional plane of the set of cross-sectional planes can be selected to coincide with a point that is the predetermined distance below the mid ascending aorta.

In some implementations, the value representing a variation in radiodensity values within the location can be determined by determining a statistical measure of dispersion, such as a range, across the defined location. Alternatively, each defined location in the aorta can be divided into a plurality of regions, and a representative radiodensity measurement can be obtained for each of the plurality of regions. For example, an average radiodensity value for each region can be calculated. The value representing the variation in radiodensity can be calculated from the representative radiodensity measurements for the plurality of regions. This can be done, for example, by measuring a statistical measure of dispersion across the representative values for each region. In one example, the value representing the variation in radiodensity is calculated by determining a maximum variation between any two of the representative radiodensity measurements for the plurality of regions.

At 306, a parameter representing a likelihood that the patient is experiencing an acute aortic syndrome (AAS) is determined, at a derived model from at least the set of variation values. In some implementations, the derived model can also use a set of at least one clinical parameter associated with the patient, such as age, sex, aortic diameter, blood pressure, and a parameter representing a medical history of the patient in identify an AAS from CT images. The parameter can represent the presence of an AAS or a type, class, or location of an AAS. In one example, the parameter represents the likelihood that the patient is experiencing an acute aortic syndrome related to changes in the ascending aorta. The derived model can be any appropriate statistical or machine learning model that uses a statistical aggregation of data from patients having known clinical outcomes to predict an unknown outcome for a patient from one or more values extracted from one or more CT images of the patient. In one example, the derived model is a decision tree, and the parameter representing the likelihood that the patient is experiencing an acute aortic syndrome is a categorical parameter. At 308, the parameter representing the likelihood that the patient is experiencing the acute aortic syndrome is provided to a user at an associated output device.

FIG. 4 illustrates another example of a method 400 for automated identification of acute aortic syndromes (AASs) in computed tomography images. At 402, a region of interest in a chest of a patient is imaged via a computed tomography (CT) scanner to provide a set of cross-sectional image planes within the patient's aorta. At 404, each cross-sectional plane is divided into a plurality of regions. It will be appreciated that the regions can be of unequal size and different shapes, with the specific shapes and sizes of the regions being at least in part a function of the cross-sectional profile of the aorta at the selected location for the cross-sectional plane.

At 406, an average Hounsfield unit (HU) value is determined for each of the plurality of regions in each cross-sectional image plane. At 408, a range across the plurality of average HU values for each cross-sectional image plane is determined. Effectively, the range value representing each cross-sectional image plane is the difference between the highest average HU value for a region in the cross-sectional image plane and the lowest average HU value for a region in the cross-sectional image plane. A maximum range, RMAX, is selected across the plurality of cross-sectional planes at 410. At 412, it is determined if the maximum range exceeds a threshold value. If so (Y), it is determined that the patient is likely to have an AAS, and the patient is transferred to a specialty care facility at 414. Otherwise (N), it is determined that it is unlikely that the patient has an AAS, and the method terminates.

Figure 5:
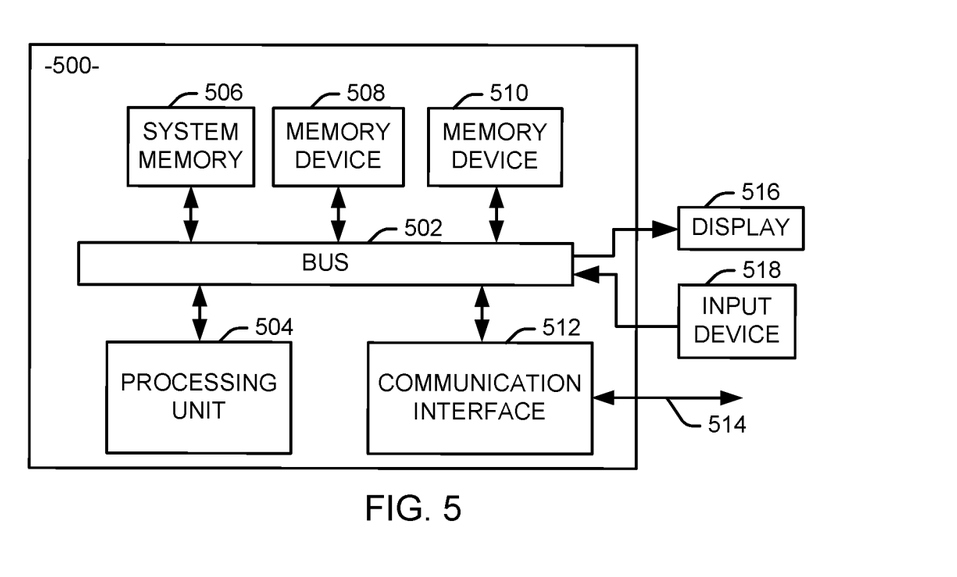
FIG. 5 is a schematic block diagram illustrating an exemplary system of hardware components that can be used to implement the systems and methods disclosed herein.

FIG. 5 is a schematic block diagram illustrating an exemplary system 500 of hardware components capable of implementing examples of the systems and methods disclosed herein. The system 500 can include various systems and subsystems. The system 500 can be a personal computer, a laptop computer, a workstation, a computer system, an appliance, an application-specific integrated circuit (ASIC), a server, a server BladeCenter, a server farm, etc.

The system 500 can include a system bus 502, a processing unit 504, a system memory 506, memory devices 508 and 510, a communication interface 512 (e.g., a network interface), a communication link 514, a display 516 (e.g., a video screen), and an input device 518 (e.g., a keyboard, touch screen, and/or a mouse). The system bus 502 can be in communication with the processing unit 504 and the system memory 506. The additional memory devices 508 and 510, such as a hard disk drive, server, standalone database, or other non-volatile memory, can also be in communication with the system bus 502. The system bus 502 interconnects the processing unit 504, the memory devices 506-510, the communication interface 512, the display 516, and the input device 518. In some examples, the system bus 502 also interconnects an additional port (not shown), such as a universal serial bus (USB) port.

The processing unit 504 can be a computing device and can include an application-specific integrated circuit (ASIC). The processing unit 504 executes a set of instructions to implement the operations of examples disclosed herein. The processing unit can include a processing core.

The additional memory devices 506, 508, and 510 can store data, programs, instructions, database queries in text or compiled form, and any other information that may be needed to operate a computer. The memories 506, 508 and 510 can be implemented as computer-readable media (integrated or removable), such as a memory card, disk drive, compact disk (CD), or server accessible over a network. In certain examples, the memories 506, 508 and 510 can comprise text, images, video, and/or audio, portions of which can be available in formats comprehensible to human beings.

Additionally or alternatively, the system 500 can access an external data source or query source through the communication interface 512, which can communicate with the system bus 502 and the communication link 514.

In operation, the system 500 can be used to implement one or more parts of a system for automated identification of acute aortic syndromes in computed tomography images in accordance with the present invention. Computer executable logic for implementing the system resides on one or more of the system memory 506, and the memory devices 508 and 510 in accordance with certain examples. The processing unit 504 executes one or more computer executable instructions originating from the system memory 506 and the memory devices 508 and 510. The term "computer readable medium" as used herein refers to a medium that participates in providing instructions to the processing unit 504 for execution. This medium may be distributed across multiple discrete assemblies all operatively connected to a common processor or set of related processors. Specific details are given in the above description to provide a thorough understanding of the embodiments. However, it is understood that the embodiments can be practiced without these specific details. For example, physical components can be shown in block diagrams in order not to obscure the embodiments in unnecessary detail. In other instances, well-known circuits, processes, algorithms, structures, and techniques can be shown without unnecessary detail in order to avoid obscuring the embodiments.

Implementation of the techniques, blocks, steps and means described above can be done in various ways. For example, these techniques, blocks, steps and means can be implemented in hardware, software, or a combination thereof. For a hardware implementation, the processing units can be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, other electronic units designed to perform the functions described above, and/or a combination thereof.

Also, it is noted that the embodiments can be described as a process which is depicted as a flowchart, a flow diagram, a data flow diagram, a structure diagram, or a block diagram. Although a flowchart can describe the operations as a sequential process, many of the operations can be performed in parallel or concurrently. In addition, the order of the operations can be re-arranged. A process is terminated when its operations are completed, but could have additional steps not included in the figure. A process can correspond to a method, a function, a procedure, a subroutine, a subprogram, etc. When a process corresponds to a function, its termination corresponds to a return of the function to the calling function or the main function.

Furthermore, embodiments can be implemented by hardware, software, scripting languages, firmware, middleware, microcode, hardware description languages, and/or any combination thereof. When implemented in software, firmware, middleware, scripting language, and/or microcode, the program code or code segments to perform the necessary tasks can be stored in a machine readable medium such as a storage medium. A code segment or machine-executable instruction can represent a procedure, a function, a subprogram, a program, a routine, a subroutine, a module, a software package, a script, a class, or any combination of instructions, data structures, and/or program statements. A code segment can be coupled to another code segment or a hardware circuit by passing and/or receiving information, data, arguments, parameters, and/or memory contents. Information, arguments, parameters, data, etc. can be passed, forwarded, or transmitted via any suitable means including memory sharing, message passing, ticket passing, network transmission, etc.

For a firmware and/or software implementation, the methodologies can be implemented with modules (e.g., procedures, functions, and so on) that perform the functions described herein. Any machine-readable medium tangibly embodying instructions can be used in implementing the methodologies described herein. For example, software codes can be stored in a memory. Memory can be implemented within the processor or external to the processor. As used herein the term "memory" refers to any type of long term, short term, volatile, nonvolatile, or other storage medium and is not to be limited to any particular type of memory or number of memories, or type of media upon which memory is stored.

Moreover, as disclosed herein, the term "storage medium" can represent one or more memories for storing data, including read only memory (ROM), random access memory (RAM), magnetic RAM, core memory, magnetic disk storage mediums, optical storage mediums, flash memory devices and/or other machine readable mediums for storing information. The term "machine-readable medium" includes, but is not limited to portable or fixed storage devices, optical storage devices, wireless channels, and/or various other storage mediums capable of storing that contain or carry instruction(s) and/or data.

What have been described above are examples. It is, of course, not possible to describe every conceivable combination of components or methodologies, but one of ordinary skill in the art will recognize that many further combinations and permutations are possible. Accordingly, the disclosure is intended to embrace all such alterations, modifications, and variations that fall within the scope of this application, including the appended claims. As used herein, the term "includes" means includes but not limited to, the term "including" means including but not limited to. The term "based on" means based at least in part on. Additionally, where the disclosure or claims recite "a," "an," "a first," or "another" element, or the equivalent thereof, it should be interpreted to include one or more than one such element, neither requiring nor excluding two or more such elements.

What is claimed is:

1. A method comprising:
   imaging a region of interest in a chest of a patient via a computed tomography (CT) scanner to provide images at a plurality of locations, the region of interest including one of an ascending aorta, an aortic arch, and a descending aorta of the patient;
   determining, for each of the plurality of locations within the region of interest, a value representing a variation in radiodensity values within the location from the image to provide a set of variation values, the plurality of locations including a set of cross-sectional planes within one of the ascending aorta, the aortic arch, and the descending aorta, and the set of cross-sectional planes including a first cross-sectional plane selected to coincide with a mid-ascending aorta, a second cross-sectional plane selected to coincide with a point that is a first predetermined distance above the mid ascending aorta, and a third cross-sectional plane selected to coincide with a point that is a second predetermined distance below the mid ascending aorta;
   determining, at a derived model, a parameter representing a likelihood that the patient is experiencing an acute aortic syndrome from the set of variation values; and
   providing the parameter representing the likelihood that the patient is experiencing the acute aortic syndrome to a user at an associated output device.

2. The method of claim 1, wherein each of the set of the variation values for each of the plurality of locations include a range of representative radiodensity values within the location.

3. The method of claim 1, wherein determining the parameter representing the likelihood that the patient is experiencing an acute aortic syndrome includes determining a parameter representing the likelihood that the patient is experiencing an acute aortic syndrome related to changes in the ascending aorta.

4. The method of claim 1, wherein determining the value representing the variation in radiodensity values within each of the plurality of locations comprises, for each of the set of cross-sectional planes:
   dividing the aorta into a plurality of regions;
   obtaining a representative radiodensity measurement for each of the plurality of regions; and
   calculating the value representing the variation in radiodensity from the representative radiodensity measurements for the plurality of regions.

5. The method of claim 4, wherein calculating the value representing the variation in radiodensity values comprises determining a maximum variation between any two of the representative radiodensity measurements for the plurality of regions.

6. The method of claim 4, wherein obtaining a representative radiodensity measurement for each of the plurality of regions comprises calculating an average radiodensity value across at least a portion of the region.

7. The method of claim 1, wherein the derived model is a decision tree, and the parameter representing the likelihood that the patient is experiencing an acute aortic syndrome is a categorical parameter.

8. The method of claim 1, wherein determining the parameter representing the likelihood that the patient is experiencing an acute aortic syndrome from the set of variation values comprises determining the parameter representing the likelihood that the patient is experiencing an acute aortic syndrome from the set of variation values and a set of at least one clinical parameter associated with the patient.

9. The method of claim 8, wherein the set of at least one clinical parameter comprises one of age, sex, aortic diameter, blood pressure, and a parameter representing a medical history of the patient.

10. A system comprising:
    a processor; and
    a non-transitory computer readable medium storing executable instructions executable by the processor to provide:
       a scanner interface that receives a computed tomography (CT) image of a region of interest in a chest of a patient from a CT scanner, the region of interest including one of the ascending aorta, aortic arch, and descending aorta of the patient;
       a feature extractor that determines, for each of a plurality of locations within the region of interest, a value representing a variation in radiodensity values within the location from the CT image to provide a set of variation values, the feature extractor determining the value representing a variation in radiodensity values within each of a set of cross-sectional planes within one of the ascending aorta, the aortic arch, and the descending aorta, the set of cross-sectional planes including a first cross-sectional plane selected to coincide with a mid-ascending aorta, a second cross-sectional plane selected to coincide with a point that is a first predetermined distance above the mid ascending aorta, and a third cross-sectional plane selected to coincide with a point that is a second predetermined distance below the mid ascending aorta;
       a derived model that determines, from at least the set of variation values, a parameter representing a likelihood that the patient is experiencing an acute aortic syndrome; and a user interface that provides the parameter presenting the likelihood that the patient is experiencing the acute aortic syndrome to an associated output device.

11. The system of claim 10, wherein the feature extractor determines the value representing a variation in radiodensity values within each of the plurality of locations as a range of representative radiodensity values within the location.

12. The system of claim 10, wherein the feature extractor determines the representative radiodensity measurement for each of the plurality of regions as an average radiodensity value for a subregion lying entirely within the region.

13. The system of claim 10, wherein the derived model is a machine learning model.

14. The system of claim 10, wherein the feature extractor determines the value representing a variation in radiodensity values within each of the plurality of locations as an inter-quartile range of representative radiodensity values within the location.

15. The system of claim 10, wherein the feature extractor determines the value representing a variation in radiodensity values within each of the plurality of locations as a standard deviation of representative radiodensity values within the location.

16. The system of claim 15, wherein the feature extractor determines the range value for representative HU values within each of the plurality of locations by determining representative HU measurements for each of a plurality of regions within each location and calculating the range value for each location from the representative HU measurements for the plurality of regions.

17. A system comprising:
a computed tomography (CT) scanner;
a processor; and
a non-transitory computer readable medium storing executable instructions executable by the processor to provide:
a scanner interface that receives a CT image of a region of interest in a chest of a patient from the CT scanner, the region of interest including one of the ascending aorta, aortic arch, and descending aorta of the patient;
a feature extractor that determines, for each of a plurality of locations within the region of interest, a range of representative Hounsfield unit (HU) values within the location from the CT image to provide a set of range values, the feature extractor determining the value representing a variation in radiodensity values within each of a set of cross-sectional planes within one of the ascending aorta, the aortic arch, and the descending aorta, the set of cross-sectional planes including a first cross-sectional plane selected to coincide with a mid-ascending aorta, a second cross-sectional plane selected to coincide with a point that is a first predetermined distance above the mid ascending aorta, and a third cross-sectional plane selected to coincide with a point that is a second predetermined distance below the mid ascending aorta;
a derived model that determines, from at least the set of range values, a parameter representing a likelihood that the patient is experiencing an acute aortic syndrome; and
a user interface that provides the parameter presenting the likelihood that the patient is experiencing the acute aortic syndrome to an associated output device.

* * * * *